United States Patent [19]

Davis et al.

[11] Patent Number: 5,095,619
[45] Date of Patent: Mar. 17, 1992

[54] SHAVING SYSTEM

[75] Inventors: Iris J. Davis, Gaithersburg, Md.; Brian A. Rogers, South Boston; Mingchih M. Tseng, Hingham, both of Mass.

[73] Assignee: The Gillette Company, Boston, Mass.

[21] Appl. No.: 589,674

[22] Filed: Sep. 28, 1990

[51] Int. Cl.$^5$ .............. B26B 21/00; B26B 19/44; B26B 21/40; A61K 7/15
[52] U.S. Cl. ............................... 30/41; 30/50; 30/90; 424/73
[58] Field of Search .............. 30/34.05, 50, 41, 90, 30/84; 83/14; 424/73

[56] References Cited

U.S. PATENT DOCUMENTS

| | | | |
|---|---|---|---|
| 4,170,821 | 10/1979 | Booth . | |
| 4,381,293 | 4/1983 | Michel | 30/90 |
| 4,501,834 | 2/1985 | Su | 424/73 |
| 4,586,255 | 5/1986 | Jacobson . | |
| 4,624,051 | 11/1986 | Apprille . | |
| 4,850,106 | 7/1989 | Braun et al. | 30/41 |
| 4,858,314 | 8/1989 | Cunningham | 30/41 |
| 4,872,263 | 10/1989 | Etheridge . | |
| 4,875,287 | 10/1989 | Creasy . | |
| 4,954,337 | 9/1990 | Gripp et al. | 424/73 |

FOREIGN PATENT DOCUMENTS 2024082 5/1982 United Kingdom .

Primary Examiner—Douglas D. Watts
Assistant Examiner—Paul M. Heyrana, Sr.
Attorney, Agent, or Firm—Fish & Richardson

[57] ABSTRACT

A shaving unit that comprises at least one blade and a shaving composite has a surface for engaging the user's skin adjacent the blade edge. The shaving unit may be of a disposable cartridge type adapted for coupling to and uncoupling from a razor handle or may be integral with a handle so that the complete razor is discarded as a unit when the blade or blades become dulled. The blade edge (or edges) cooperate with skin engaging surfaces to define shaving geometry. The skin-engaging surface includes a shaving aid composite that is a mixture of water insoluble matrix material, an effective amount of shaving aid material, and an effective amount of water-insoluble essential oil material, the water-insoluble essential oil material being delivered from the shaving aid composite concurrently with the delivery of the water-leachable shaving aid material during shaving to apply at least about one nanogram of the essential oil to the skin surface per square centimeter of skin surface.

16 Claims, 1 Drawing Sheet

SHAVING SYSTEM

This invention relates to shaving systems, and more particularly to shaving systems of the wet shave type.

In shaving systems of the wet shave type, factors such as the frictional drag of the razor across the skin, the force needed to sever hairs, and irritation of pre-existing skin damage can create a degree of shaving discomfort. Discomfort, and other problems accompanying wet shaving systems, can be alleviated by the application of shaving aids to the skin. Shaving aids may be applied prior to, during, or after shaving. A number of problems accompany the use of pre- and post-applied shaving aids. Pre-applied-shaving aids can evaporate or can be carried away from the site of application by repeated strokes of the razor. Post-applied-shaving aids are not present on the skin during shaving and thus their application may be to late to prevent an unwanted affect. Both pre-applied and post-applied shaving aids add additional steps to the shaving process.

Proposals have been made to incorporate a shaving aid e.g., lubricant, whisker softener, razor cleanser, medicinal agent, cosmetic agent or combination thereof, into a razor, e.g., by frictionally securing a shaving aid in a recess on the razor, by incorporating a shaving aid directly into one or more molded polymeric components of the razor, by adhesively securing a shaving aid composite to the razor, and by use of a mechanical connection between a shaving aid composite and the razor. A water-soluble shaving aid, e.g. polyethylene oxide, has been mixed with non-water-soluble material, e.g., a polystyrene polymer, to form an insoluble polymer/soluble shaving aid composite. The composite has been mounted on razor and shaving cartridge structures, adjacent the shaving edge or edges, of single or multiple blade shaving system. Upon exposure to water, the water-soluble shaving aid leaches from the composite onto the skin.

In accordance with one aspect of the invention, there is provided a shaving unit that comprises at least one blade and a shaving composite that has a surface for engaging the user's skin adjacent the blade edge. The shaving unit may be of a disposable cartridge type adapted for coupling to and uncoupling from a razor handle or may be integral with a handle so that the complete razor is discarded as a unit when the blade or blades become dulled. The blade edge (or edges) cooperate with skin engaging surfaces to define shaving geometry. The skin-engaging surface includes a shaving aid composite that is a mixture of water insoluble matrix material, an effective amount of shaving aid material, and an effective amount of water-insoluble essential oil material, the water-insoluble essential oil material being delivered from the shaving aid composite concurrently with the delivery of the water-leachable shaving aid material during shaving to apply at least about one nanogram of the essential oil to the skin surface per square centimeter of skin surface.

Preferably, the shaving aid composite is of estrusion-oriented material, and comprises 20–40% by weight of the matrix material, 40–75% by weight of the water-leachable shaving aid material, and 2–20% by weight of the essential oil material. The shaving aid composition may further include a release enhancing agent selected from the group consisting of polyethylene glycol, methoxypolyethylene glycol, methylcellulose, and carboxypolymethylene.

Suitable water-insoluble matrix materials include, for example, polyethylene, polypropylene, polystyrene and polyacetyl. Suitable shaving aid materials include, for example, polyethylene oxide, polyvinyl pyrrolidone, polyacrylamide, hydroxypropyl cellulose, polyvinyl imidazonline, polyhydroxyethylmethacrylate, silicone copolymers, sucrose stearate, vitamin E, panthenol and aloe. Suitable essential oil materials include menthol, eugenol (oil of clove), eucalyptol (oil of eucalyptus and oil of cajeput), safrol (oil of sassafras) and methyl salicylate (oil of wintergreen).

In particular embodiments, the shaving agent composite is a member of extrusion-oriented blend of polymeric materials that contains water-soluble and water-insoluble materials, the nature and relative proportions of the water-soluble and water-insoluble polymeric materials being such that the member has adequate mechanical strength, both as initially produced and after a significant amount of the water-soluble material has been leached out.

In accordance with another aspect, there is provided a process for forming a shaped shaving aid composite for a shaving system of the wet shave type that includes a matrix of water-insoluble polymeric material, an effective amount of water-leachable shaving aid material, and an effective amount of water-insoluble essential oil material, the process including the steps of forming a blend of the water-insoluble polymeric material and the water-leachable shaving aid material, adding the water-insoluble essential oil material in particulate to form to the blend at a temperature of less than 100° C. to form a mixture, and extruding the mixture in less than one minute after the essential oil material is added to form the shaped shaving aid composite.

Other features and advantages will be seen as the following description of particular embodiments progresses, in conjunction with the drawings, in which.

DESCRIPTION OF PARTICULAR EMBODIMENTS

Figure 1:
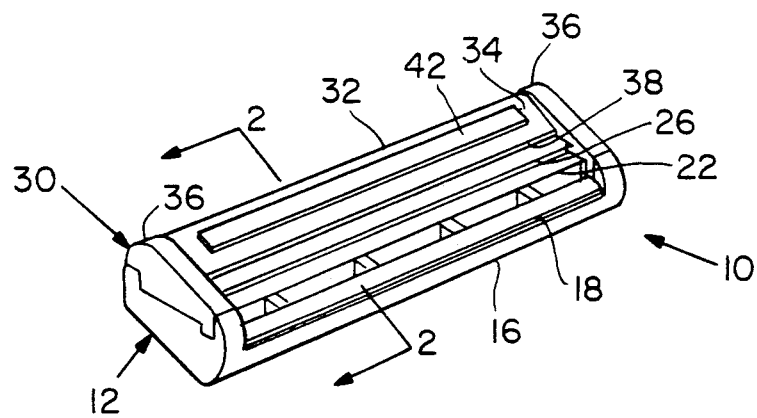
FIG. 1 is a perspective view of a razor unit in accordance with the invention.
Figure 2:
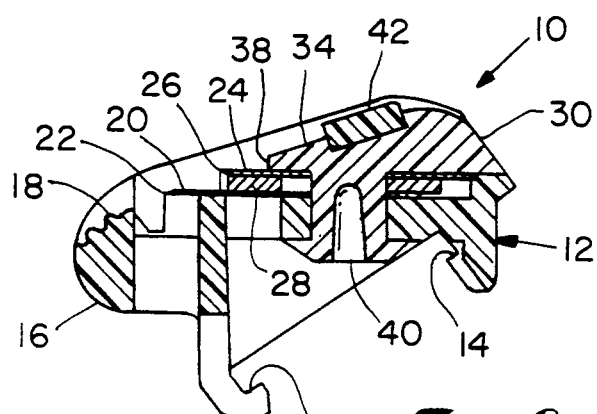
FIG. 2 is a sectional view taken along the line 2-2 of FIG. 1.

The shaving unit 10 shown in FIGS. 1 and 2 includes base or platform member 12 molded of high impact polystyrene that includes integral coupling groove structure 14 for attachment to a razor handle and guard structure 16 that defines a transversely extending forward skin engaging surface 18. On the upper surface of platform 12 are disposed steel leading blade 20 having a sharpened edge 22, steel following blade 24 having sharpened edge 26, and aluminum spacer member 28 that maintains blades 20 and 24 in spaced relation. Cap member 30 is molded of high impact polystyrene and has body portion 32 that defines skin engaging surface 34 that extends transversely between forwardly projecting end walls 36 and has a front edge 38 that is disposed rearwardly of blade edge 26. Integral rivet portions 40 extend downwardly from transversely extending body portion 32 and pass through holes in blades 20 and 24, spacer 28, and platform 12 to secure cap 30, blades 20, 24 and spacer 28 on platform 12. Adhesively affixed to skin engaging surface 34 is shaving aid composite 42.

Figure 3:
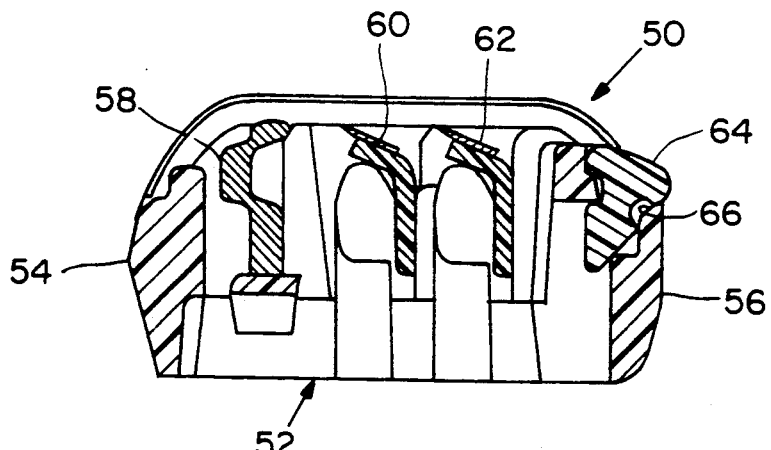
FIG. 3 is a perspective view of another razor unit in accordance with the invention.

The shaving unit 50 shown in FIG. 3 is of the type shown in Jacobson U.S. Pat. No. 4,586,255 and includes body 52 with front portion 54 and rear portion 56. Resiliently secured in body 52 are guard member 58, leading blade unit 60 and trailing blade unit 62. A shaving aid composite in the form of elongated insert member 64 is frictionally locked in opening 66 of rear portion 56.

The following examples show by way of illustration and not by way of limitation practice of the invention.

EXAMPLE 1

A blend is formed of about thirty-one percent by weight high impact polystyrene; fifty percent by weight of a water soluble polymer (specifically a mixture of sixty percent by weight Polyox Coagulant polyethylene oxide five million molecular weight and forty weight percent Polyox WSRN-750 polyethylene oxide —300,000 molecular weight); nine percent by weight of water soluble polyethylene glycol (4,500 molecular weight); and ten percent by weight of menthol. The blend includes color dye and antioxidant additives in minor amounts. The blend is extruded through a nineteen millimeter diameter screw extruder. The menthol is fed into the mixture in small particulate form (particles of about forty microns or less in size) and is mixed with the other constituents and extruded with a residence time in the extrusion system of less than one minute. The feed zone (input to the barrel) is at a temperature of about 80° C., intermediate barrel temperatures are about 130° C. and 160° C. and the die is at a temperature of about 180° C. The barrel pressure is about 1,800 psi and the die pressure is about 2,400 psi. An extruded strip member of cross sectional shape indicated in FIG. 3 is formed. Members 64 are sliced from the extruded strip and secured in openings 66 of shaving units 50. The resulting extruded member 64 is sturdy and has an attractive appearance, and the resulting cartridge 50 possesses good overall shaving performance.

EXAMPLE 2

A blend is formed of about thirty-two percent by weight high impact polystyrene; fifty-two percent by weight of a water soluble polymer (specifically a mixture of sixty percent by weight Polyox Coagulant polyethylene oxide five million molecular weight and forty weight percent Polyox WSRN-750 polyethylene oxide —300,000 molecular weight); nine percent by weight of water soluble polyethylene glycol (4,500 molecular weight); and six percent by weight of menthol. The blend includes color dye and antioxidant additives in minor amounts. The blend is extruded through an extruder. The menthol is fed into the mixture in small particulate form (particles of fifty-one hundred microns in size) and is mixed with the other constituents. The water-cooled feed zone (input to the barrel) is at a temperature of about 17° C., intermediate barrel temperatures are about 120° C. and 160° C. and the die is at a temperature of about 160° C. The barrel pressure is about 2,700 psi and the die pressure is about 1,900 psi. An extruded strip member of cross sectional shape indicated in FIG. 3 is formed. Members 64 are sliced from the extruded strip and secured in openings 66 of shaving units 50. The resulting extruded member 64 is sturdy and has an attractive appearance, and the resulting cartridge 50 possesses good overall shaving performance.

EXAMPLE 3

A blend is formed of about thirty-one percent by weight high impact polystyrene; fifty percent by weight of a water soluble polyethylene oxide; nine percent by weight of water soluble polyethylene glycol (4,500 molecular weight); and ten percent by weight of menthol. The blend is extruded through an extruder. The menthol is fed into the mixture in small particulate form and is mixed with the other constituents and extruded with a residence time in the extrusion system of less than one minute. The feed zone (input to the barrel) is at a temperature of about 120° C., the barrel temperature is about 160° C. and the die is at a temperature of about 160° C.. An extruded strip member of cross sectional shape indicated in FIG. 3 is formed. Members 64 are sliced from the extruded strip and secured in openings 66 of shaving units 50. The resulting extruded member 64 is sturdy and has an attractive appearance, and the resulting cartridge 50 possesses good overall shaving performance.

EXAMPLE 4

A blend is formed of about twenty-seven percent by weight high impact polystyrene; forty-five percent by weight of water-soluble polyethylene oxide; eight percent by weight of water-soluble polyethylene glycol (4,500 molecular weight); and twenty percent by weight of menthol. The blend is extruded through an extruder, and the menthol is fed into the mixture in small particulate form and is mixed with the other constituents and extruded with a residence time in the extrusion system of less than one minute. The feed zone (input to the barrel) is at a temperature of about 80° C., the barrel temperature is about 160° C. and the die is at a temperature of about 180° C. An extruded strip member of cross sectional shape indicated in FIG. 3 is formed. Members 64 are sliced from the extruded strip and secured in openings 66 of shaving units 50. The resulting extruded member 64 is sturdy and has an attractive appearance, and the resulting cartridge 50 possesses good overall shaving performance.

The water-insoluble menthol is dispersed from the cartridge insert with the polyethylene oxide lubricant and tends to reduce the level of irritation produced upon shaving and to improve the overall comfort and quality of the shave. The resulting quantity of the menthol in insert 64 is about three percent, a portion of which is associated with the polystyrene and about twenty percent of the original quantity of the menthol in the insert member remains with the polystyrene residue after the polyethylene oxide and other water-extractable materials have been completely leached from insert 64.

The system delivers about fifteen nanograms of menthol per square centimeter of the skin and about two-thirds of the delivered menthol is substantive. Inserts 64 containing about three percent menthol were shown to deliver about five micrograms of menthol to the face during shaving (as determined by gas chromatography/mass spectrometry, analysis of alcohol extracts of the skin surface). After rinsing, about two-thirds of the delivered menthol; i.e., 3.3 micrograms, remained on the skin.

While particular embodiments of the invention have been shown and described, various modifications will be apparent to those skilled in the art and therefore it is not intended that the invention be limited to the disclosed embodiment or to details thereof and departures may be made therefrom within the spirit and scope of the invention.

What is claimed is:

1. A shaving system of the wet shave type comprising a blade member, and structure defining an external skin-engaging portion adjacent the shaving edge of said blade member, said skin-engaging portion including a shaped shaving aid composite that includes a matrix of water-insoluble polymeric material, an effective amount of water-leachable shaving aid material, and an effective amount of water-insoluble essential oil material, said water-insoluble essential oil material being delivered from said shaving aid composite concurrently with the delivery of said water-leachable shaving aid material during shaving to apply at least about one nanogram of said essential oil to the skin surface per square centimeter of skin surface.

2. The shaving system of claim 1 wherein said essential oil is selected from the group consisting of menthol, eugenol, eucalyptol, safrol and methyl salicylate.

3. The shaving system of claim 1 wherein said shaving aid composite further includes a release enhancing agent selected from the group consisting of polyethylene glycol, methoxypolyethylene glycol, methylcellulose, and carboxypolymethylene.

4. The shaving aid system of claim 3 wherein the molecular weight of said release enhancing agent is less than one percent of the molecular weight of said shaving aid material.

5. The shaving system of claim 1 wherein said shaving aid composite is of extrusion-oriented material.

6. The shaving system of claim 1 wherein said polymeric matrix material is selected from the group consisting of polyethylene, polypropylene, polystyrene, and polyacetyl; and said shaving aid material is selected from the group consisting of polyethylene oxide, polyvinyl pyrrolidone, polyacrylamide, hydroxypropyl cellulose, polyvinyl imidazonline, polyhydroxyethylmethacrylate, silicone polymers, sucrose stearate, vitamin E, panthenol, and aloe.

7. The shaving system of claim 1 wherein said shaving aid composite comprises 20–40% by weight of said matrix material, 40–75% by weight of said water-leachable shaving aid material, and 2–20% by weight of said essential oil material.

8. The shaving system of claim 7 wherein said essential oil is selected from the group consisting of menthol, eugenol, eucalyptol, safrol and methyl salicylate.

9. The shaving system of claim 8 wherein said shaving aid composite is of extrusion-oriented material.

10. The shaving system of claim 9 wherein said polymeric matrix material is selected from the group consisting of polyethylene, polypropylene, polystyrene, and polyacetyl; and said shaving aid material is selected from the group consisting of polyethylene oxide, polyvinyl pyrrolidone, polyacrylamide, hydroxypropyl cellulose, polyvinyl imidazonline, polyhydroxyethylmethacrylate, silicone polymers, sucrose stearate, vitamin E, panthenol, and aloe.

11. A process for forming a shaped shaving aid composite for a shaving system of the wet shave type that includes a matrix of water-insoluble polymeric material, an effective amount of water-leachable shaving aid material, and an effective amount of water-insoluble essential oil material, comprising the steps of forming a blend of said water-insoluble polymeric material and said water-leachable shaving aid material, adding said water-insoluble essential oil material in particulate form to said blend at a temperature of less than 100° C. to form a mixture and extruding said mixture to form said shaped shaving aid composite.

12. The process of claim 11 wherein said essential oil material is menthol in particles of less than one hundred micron size.

13. The process of claim 11 wherein said essential oil material is added to said blend at a temperature of less than about 80° C.

14. The process of claim 11 wherein said essential oil material is present in said shaving aid composite in an amount less than six percent by weight.

15. The process of claim 11 wherein said essential oil material is selected from the group consisting of menthol, eugenol, eucalyptol, sarfrol and methyl salicylate.

16. The process of claim 15 wherein said essential oil material is added to said blend as particles of less than one hundred micron size at a temperature of less than 80° C., and said essential oil material is present in said shaving aid composite in an amount of about three percent by weight.

* * * * *